United States Patent [19]

Morrison et al.

[11] Patent Number: 5,489,745
[45] Date of Patent: Feb. 6, 1996

[54] HIGH PIGMENT, REDUCED BLOSSOM END SCAR SIZE, DISEASE RESISTANT TOMATO VARIETIES

[75] Inventors: Robert A. Morrison; David A. Evans, both of Cinnaminson, N.J.

[73] Assignee: DNA Plant Technology Corporation, Oakland, Calif.

[21] Appl. No.: 145,543

[22] Filed: Nov. 4, 1993

Related U.S. Application Data

[63] Continuation of Ser. No. 876,839, Apr. 30, 1992, which is a continuation-in-part of Ser. No. 769,309, Oct. 1, 1991, abandoned, which is a continuation of Ser. No. 638,259, Jan. 4, 1991, abandoned, which is a continuation of Ser. No. 291,800, Dec. 29, 1988, abandoned.

[51] Int. Cl.$^6$ .............................. A01H 5/00; A01H 5/10; A01H 4/00; C12N 5/04
[52] U.S. Cl. ..................... 800/200; 800/230; 800/255; 800/DIG. 44; 435/240.51
[58] Field of Search ................................... 800/200, 230, 800/DIG. 44, 255; 435/240.51

[56] References Cited

U.S. PATENT DOCUMENTS

| P.P. 2,656 | 7/1966 | Wicks | Plt./89 |
|---|---|---|---|
| P.P. 4,539 | 5/1980 | Briggs | Plt./89 |
| P.P. 5,171 | 1/1984 | Briggs | Plt./89 |
| P.P. 5,812 | 11/1986 | Pezzulia | Plt./89 |
| 4,843,186 | 6/1989 | Nahum | 800/1 |

OTHER PUBLICATIONS

Stokes Seed Company Catalogue, 1990, entries 404B (Crimsonvee VF), 403C (Earlibright), 372 (Earlirouge), 362A (Moira), 328 (Quinte), 325A (Super Stokesdale), 403A (Bonyvee), and 403B (Harvestvee).

Tomato Genetics Cooperative Report 1987, No. 37, p. 90.

PVP Certificate No. 8400146 for cultivar DNAP-9 (1986), pp. 1–13.

Scott et al., 1985, Suncoast Circular S-322, Agricultural Experimental Station University of Florida, Gainsville.

Metcalf et al., 1985, Hort. Sci. 20:788.

Wann et al., 1985, J. Amer. Soc. Hort. Sci. 110:212–215.

Sayama et al., 1985, Japan J. Breeding 35:145–152.

Kerr, 1983, Can. J. Plant Sci. 63:769–770.

Tomato Genetics Cooperative Report 1981, No. 31, pp. 45–46.

Kerr and Cook, 1979, Can. J. Plant Sci. 59:895–896.

Thompson, 1961, Am. Soc. Hort. Sci. 78:464–473.

Germplasm Resources Information Network (GRIN); Agricultural Research Service, USDA, Beltsville, MD, Printout of 40 Plant Introductions.

Sikes et al., 1976, Hort. Science 11(1):26–27.

Elkind et al 1990 Euphytica 50:91–95.

*Primary Examiner*—Patricia R. Moody
*Attorney, Agent, or Firm*—Pennie & Edmonds

[57] ABSTRACT

The present invention provides novel tomato lines having disease resistance, and producing a tomato(es) having a weight of at least 140 g with high pigment and reduced blossom end scar size relative to "Suncoast". Due to the reduced blossom end scar size, the tomatoes of the present invention have an increased marketable yield relative to "Suncoast".

1 Claim, 2 Drawing Sheets

101-33

SUNCOAST 103-114

103

HIGH PIGMENT, REDUCED BLOSSOM END SCAR SIZE, DISEASE RESISTANT TOMATO VARIETIES

This is a continuation of application Ser. No. 07/876,839, filed Apr. 30, 1992, now pending; which is a Continuation In Part (CIP) of Ser. No. 07/769,309, filed Oct. 1, 1991, now abandoned; which was a Continuation of Ser. No. 07/638,259, filed Jan. 4, 1991, now abandoned; which was a Continuation of Ser. No. 07/291,800, filed Dec. 29, 1988, now abandoned.

TABLE OF CONTENTS

1. Field of the Invention
2. Background of the Invention
   2.1. Breeding Goals In Tomato
   2.2. Somaclonal Variation
   2.3. Tomato Somaclonal Variants
3. Brief Description of the Figures
4. Summary of the Invention
5. Detailed Description of the Invention
   5.1. Source Material
      5.1.1. Suncoast Somaclones
      5.1.2. Line 103 Somaclones
      5.1.3. Somaclonal Variation
   5.2. High Pigment
   5.3. Reduced Blossom End Scar Size
   5.4. Increased Number of Marketable Fruit
   5.5. Disease Resistance
   5.6. Use of the Tomatoes of the Invention as Source Material for Somaclonal Variation and as Parents in Hybrid Crosses
6. Example
   6.1. Somaclonal Variation
   6.2. Selection of 101–33
   6.3. Selection of 103–114

1. Field of the Invention

The cultivated tomato, *Lycopersicon esculentum*, is one of the most important vegetable crops in the United States and worldwide, with several million tons being produced each year in the United States alone. The commercial importance of the crop has necessitated a constant effort to improve the cultivated varieties, both by traditional breeding methods and by the more recently developed in vitro tissue culture techniques. Selection of favored characteristics are not limited to agronomic traits, such as higher yield and disease resistance; also important is selection for consumer-oriented improvements in fruit size, color, flavor and texture. Significant developments in crop improvement of any kind require the development of new varieties having characteristics or combinations of characteristics which have not been previously found in any single cultivated line. Success in development of new varieties and new traits in cultivated tomato has been to some extent hampered by the fact that *L. esculentum* has been somewhat refractory to cross-breeding with wild-type species, such as *L. peruvianum* or *L. pennellii*; it is frequently these closely related wild species which possess useful characteristics, such as disease resistance, which have been bred out of the cultivated lines over the years. The relative difficulty experienced in producing viable hybrids with improved features by traditional breeding methods has made development of new tomato varieties using in vitro techniques even more important. Unfortunately, cultivated tomato is also not particularly amenable to regeneration in tissue culture, and this too has to some extent hampered the progress of isolation of desirable variants and the development of useful variant lines. In connection with the present invention, however, the phenomenon of somaclonal variation has been successfully employed in the development of a new type of tomato having improved fruit characteristics, disease resistance, reduced blossom end scar size, and increased marketable yield.

2. Background of the Invention

2.1. BREEDING GOALS IN TOMATO

Tomatoes produced in the United States are typically used for a variety of different purposes, and therefore, development of different varieties having features adapted for a particular end use, is one of the major goals of tomato breeders. For example, the largest proportion of tomatoes produced are used for processing, e.g., for juices, soups, sauces or other tomato-based products in which the tomato undergoes some degree of alteration before being presented to the consumer. A smaller, but significant portion of the overall tomato crop produced in the United States are fresh market tomatoes, i.e., those which appear on supermarket shelves and are purchased as fresh produce by the consumer.

Needless to say, the qualities which would be desirable in a processing tomato are not necessarily those which would be desirable in a fresh market tomato; thus, the selection process for suitable varieties for each specific end use will necessarily be different as well. Of course, certain traits, such as disease and pest resistance, high yield and concentrated fruit set are of interest in any type of tomato line. However, certain features, such as solids content, which are the constituent components of tomato fruit other than water, and small and firm fruit (to facilitate mechanical harvesting) are more actively sought in development of processing tomato lines.

On the other hand, superficial, external features such as intensity and uniformity of fruit color, unblemished fruit, and larger but uniform fruit size are typically more important to the development of a fresh market product which will have consumer appeal. Intensely and uniformly red tomatoes in the prior art have been found to contain the crimson ($og^c$) and/or high pigment (hp) allele (Sayama and Tigchelar, 1985, Japan J. Breed. 35:145–152). Attempts to obtain intensely red tomatoes have had only limited success. Although high-pigment tomatoes are not unknown, they have been largely restricted to use as home-grown varieties, and are not available on a large-scale, commercial basis, primarily because of the relatively low yields that tend to be associated with this trait. This is particularly true of tomatoes carrying the hp allele, which produces an excellent red color, but which also has a number of undesirable pleiotropic effects associated with it, such as slow germination and growth, and premature defoliation.

Efforts to obtain new variants having the desired characteristics as the basis for development of new varieties has to a large extent focused on attempts to obtain interspecific hybrids, particularly with the wild species *L. chilense*, and *L. peruvianum*. These two species have been thought to hold a great deal of promise in development of new cultivated varieties, as they both contain a number of valuable traits which would theoretically prove useful in improving the cultivated variety. *L. peruvianum*, for example, is known to contain genes for resistance to numerous tomato diseases and root knot nematode, as well for high vitamin C content. Unfortunately, obtaining hybrids between the cultivated tomato and the wild species *L. peruvianum* has been severely hampered by strong interspecific incompatibilities. Through hybridization by traditional methods between these two species, fruits are only obtained if *L. esculentum* is the female parent, and even with this control, it is necessary to employ embryo culture to establish seedlings. The laborious and tedious manipulations required with hand pollination and embryo culture have thus far prevented traditional breeding methods from being a valuable means of obtaining genetic variation in *L. esculentum*.

2.2. SOMACLONAL VARIATION

The phenomenon known as somaclonal variation has recently provided a source for development of variant plant lines. In theory, the regeneration of tissue explants into a mature plant should result in the production of clones of the parent plant, i.e., plants which are identical in genotype and phenotype to the plant from which the explant was obtained. In practice, this is in fact the result observed in the vast majority of cases. However, it has long been recognized that occasional abnormalities occur, resulting in variant plants which were generally discussed as "artifacts" of the tissue culture process. In more recent years, it has become apparent that, rather than being an unexplainable aberration in an otherwise uniform regeneration process, the appearance of variants in tissue culture may be a routine occurrence for certain types of plants and/or specific explant sources. Even more recently, it has been recognized that the existence of this phenomenon potentially provides a source of useful variation which can form the basis of developing agriculturally useful variant plant lines.

The types of variation which are frequently observed may differ from species to species, and it is often difficult to determine the genetic nature of the observed variation. One of the more frequent types of variation is a difference in chromosome number, i.e., aneuploidy, polyploidy, or mixoploidy. Chromosome changes are known to occur in high frequency in the early stages of callus or liquid cell culture, and therefore the occurrence of such abnormalities is not particularly surprising. It is possible, however, to select an appropriate culture medium which will enhance chromosome stability in the explant used.

Variations in chromosome number are not the only types which have been observed. Deletions and translocations have also been reported. Somaclonal variation has been shown to yield regenerated plants with altered growth habits, disease and pest resistance, fruit color or size, and leaf variegation, among others. Although original reports of somaclonal variation were limited to plants which were normally asexually propagated, it is now known that these techniques can be successfully applied to sexually propagated plants as well. It is easy to see, given the right type of stably inherited variation, that such a tool can be extremely useful in establishing improved cultivars in a wide range of different plants, with the advantage of avoiding the numerous crossings usually required to identify and establish a useful hybrid line by traditional breeding methods. Although it appears to be possible, to some extent, to induce variation by manipulation of the culture medium, it is not possible to predict what type of somaclones, if any, may be obtained by the procedure, and, at this time, there is no known way to guarantee the development of a variant of a particular type, or whether the somaclones produced will have value. In other words, the scientist is limited by what randomly occurring variation might appear in his culture; the possibility always exists, therefore, that no agriculturally useful variants will appear.

2.3. TOMATO SOMACLONAL VARIANTS

The occurrence of somaclonal variation has been reported in tomato, with a number of different types of traits appearing in regenerated plants (Evans and Sharp, *Science* 221: 949–951, 1983). Variations in chromosome number, particularly tetraploidy and aneuploidy, are known to occur. A great variety of desired nuclear gene mutations have also been observed. Certain of the mutations were recessive, and others dominant. One interesting variant obtained exhibited orange flowers and fruit, and yellow virescent leaves. These traits were determined to be controlled by a new recessive allele in a previously known gene at position 95 on the long arm of chromosome 10. Also recovered was a jointless pedicel mutant, a phenotype which had been known previously, and which, because the harvested fruit lacks an attached stem, is desirable for mechanical as well as manual harvesting. A dominant allele conferring resistance to *Fusarium oxysporum* Race 2 was also identified. Other mutations of interest include several male sterile and chlorophyll deficiencies, as well as fruit color mutations including a dominant orange and recessive yellow fruit.

Interestingly, a number of the regenerated morphological variants were recovered, having traits such as large leaf size, dark leaf color, and reduced fruit set. These bred true in the $R_1$ generation. This pattern is indicative of cytoplasmic inheritance, or plastid-encoded mutations. Thus, it is also clear that the potential exists for the isolation of tomatoes having either nuclear or cytoplasmic variant traits by the use of somaclonal variation. Unfortunately, the technique has not yet achieved widespread use, and to date, relatively few commercially useful variants have been identified. One example of a commercially valuable tomato somaclone is the variety known as "DNAP-9", an unusually high-solids tomato, protected by Plant Variety Protection Certificate No. 8400146. "DNAP 9" is a somaclone derivative of the processing variety 'UC826' which produces small (2–3 ounces; 56–84 grams) fruit which do not exhibit crimson red color due to the absence of the $og^c$ allele.

3. BRIEF DESCRIPTION OF THE FIGURES

The file of this patent contains at least one drawing executed in color. Copies of this patent with color photographs will be provided by the Patent and Trademark Office upon request and payment of necessary fee.

4. SUMMARY OF THE INVENTION

Figure 1A:
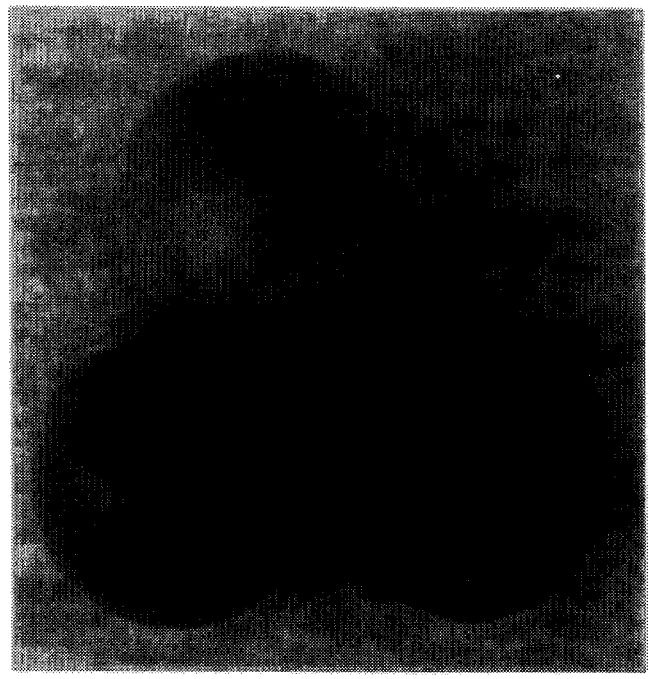
FIG. 1 shows a comparison of the blossom end scars of a tomato of the line 101–33 (top photo) and a Suncoast tomato (bottom photo).

The present invention provides plants which produce tomatoes having a novel combination of traits, specifically the characteristics of bright red color and a smooth blossom end due to reduced blossom end scar size. In one embodiment, the tomato plants produce full term tomato fruit having an average weight of at least about 140 grams, or preferably at least about 160 grams, or more preferably at least about 180 grams, or most preferably at least about 230 grams. These weights correspond respectively to fruit diameters of approximately 4.70 cm., 5.40 cm., 6.30 cm., and 7.80 cm. In another embodiment, the majority of the full term tomato fruit produced from a tomato plant of the present invention has a weight of at least about 140 grams, or preferably at least about 160 grams, or more preferably at least about 180 grams, or most preferably at least about 230 grams. In a preferred embodiment, the tomato plants of the present invention produce full term tomato fruit, each having a weight of at least about 140 grams, or preferably at least about 160 grams, or more preferably at least about 180 grams, or most preferably at least about 230 grams. "Full term tomato fruit" as defined herein are fruit which are physiologically capable of undergoing the ripening process either on their own or by virtue of treatment with ethylene.

In a specific embodiment, the bright red color may be due to the presence of the crimson ($og^c$) allele. As will be described in Section 5.2., infra, redness may be expressed as an a/b ratio where the "a" value represents the redness-greenness of the tomato, while the "b" value represents the yellowness-blueness of the tomato. The higher the a/b ratio, the redder the tomato. The tomatoes of the present invention typically have a/b ratios ranging from about 1.3 to about 2.2. Tomatoes produced by the plants of the present invention which have the $og^c$ allele generally have a/b ratios about 20–50% higher than the a/b ratios of tomatoes of known cultivars which lack the $og^c$ allele, when grown under the same environmental conditions.

Additionally, the size of the blossom end scar of the tomatoes of the present invention is substantially reduced, and generally is no greater than about 0.11 $cm^2$, preferably from about 0.03 $cm^2$ to about 0.11 $cm^2$, or alternatively no more than about 60% and generally about 25–50% of the scar size of a Suncoast tomato, grown under the same environmental conditions.

The tomato plants of the present invention are also disease resistant. Plants are said to be disease resistant if, when exposed to a specific pathogen, the plants either fail to exhibit disease symptoms or exhibit substantially reduced symptoms compared to susceptible plants. In a specific embodiment the tomatoes of the present invention are resistant to Fusarium wilt, races 1 and 2, Verticillium wilt, race 1, and Gray leaf spot caused by *Stemphylium solani*. The Ve allele confers resistance to Verticillium wilt, race 1; the $I_1$ and $I_2$ alleles confer resistance to Fusarium wilt, races 1 and 2, respectively, and the Sm allele confers resistance to Gray leaf spot caused by *Stemphylium solani*.

Furthermore, since the tomatoes of the present invention have a reduced blossom end scar size, they may also have improved marketable yield. "Marketable yield" as defined herein is the yield of tomatoes sufficiently free of defects to allow the fruit to be sold, and represents a subfraction of the total yield. Yield values are commonly expressed as pounds or tons of tomatoes per acre. A large blossom end scar detracts from a tomato's physical appearance, lessens consumer appeal, decreases marketability, and, hence lowers marketable yield values. The tomatoes of the present invention, with their strikingly reduced blossom end scars, are highly marketable and thus provide for greatly improved marketable yields compared to known cultivars.

The plants are preferably produced by the process of somaclonal variation. The invention encompasses clones, somaclones, mutaclones, gametoclones, and hybrids of such plants, as well as the seed, fruit and parts thereof, provided such clones, somaclones, mutaclones, gametoclones and hybrids retain the advantageous characteristics of the parental plants. Among the useful parts intended to be included are those which may be propagatable such as buds, flowers, leaves, stems, anthers, pollen, ovules, roots, and embryos.

5. DETAILED DESCRIPTION OF THE INVENTION

5.1. SOURCE MATERIAL

The general criteria for preferred source material include tomato lines that produce fruit with a weight of at least about 140 grams, have a bright red color according to the criteria of Section 5.2., infra, or are disease resistant.

5.1.1. SUNCOAST SOMACLONES

Some of the novel plants and tomatoes of the present invention may be developed as a somaclone of the publicly available variety known as "Suncoast" or of selections thereof (e.g. line 101). This is a large fruited, deep red tomato which is used primarily as a home garden variety (Scott, et al., University of Florida Research Bulletin (No. S-322, 1985)).

The deep red color in Suncoast is due to the presence of the $og^c$ or crimson allele. The Suncoast variety has undergone only limited commercial production primarily because of the poor marketable yields observed due to the large blossom end scar.

Other characteristics of Suncoast include a large globe to slightly flattened globe-shaped fruit, good firmness and shelf life, a high soluble solids content, and a vine with semi-determinate growth which is usually about 3–4 feet high. Suncoast is also resistant to Fusarium wilt, races 1 and 2, Verticillium wilt, and gray leafspot (*Stemphylium solani*), and is tolerant to (does not normally exhibit) blossom end rot, radial and concentric cracking, graywall, blotchy ripening, fruit pox and gold fleck. Seeds of Suncoast are available e.g., through Dr. Jay Scott, IFAS, University of Florida, AREC-Bradenton, 5007–60th Street E., Bradenton, Fla. 33508. Seeds of Suncoast have been deposited with the American Type Culture Collection under accession no. 75236.

5.1.2. LINE 103 SOMACLONES

A mixed breeding population, FL 7181, but until its disclosure herein, not to our knowledge known in the art, also has yielded somaclones within the scope of the present invention. This breeding population was also obtained from and developed by Dr. Jay Scott, and was derived from the parental lines that produced the variety Suncoast. It contains the crimson ($og^c$) allele and the same disease-resistance alleles as Suncoast. However, variations have been observed in the vine size, which is the plant size and strength (physical capacity) to hold fruit, of FL7181 plants. As will be described in further detail, infra, selections are made for uniformity in vine size, fruit size, and jointless pedicels. In a specific embodiment, the breeding line 103 is selected in the second selection. Seeds of 103 have been deposited with the American Type Culture Collection under accession no. 75235.

5.1.3. SOMACLONAL VARIATION

Due to variability in vine size and yield, the source material is first planted, open-pollinated and subjected to several selections before being entered into a program of somaclonal variation. Initial selections are made for uniformity in vine size and fruit size, and pedicel type, specifically jointless pedicels, in the case of FL7181. Additionally, in the case of FL7181, somaclones may be obtained from line 103. The methods for somaclonal variation are essentially those described in Evans et al., supra, which is incorporated herein by reference. Briefly, a somatic tissue explant, preferably leaf tissue, is removed from the selected plant line, and induced on a medium containing the appropriate combination of growth regulators (e.g. 10 micromolar ($\mu$M) 6-benzyladenine and 10 $\mu$M indole acetic acid) until callus formation is obtained. A continuous culture temperature of about 25° C. is preferred in which the plants are exposed to cool white fluorescent light of 40 $\mu$E·ms$^{-2}$ intensity for 16 hrs./day for about three to four weeks.

Shoots are regenerated from callus by transferring the callus to media comprising at least one cytokinin, such as 6-benzyladenine (6-BA), kinetin, zeatin, or 2-isopentyladenine, and at least one auxin, such as indole acetic acid (IAA), indole butyric acid (IBA), naphthalene acetic acid (NAA) or 2,4-dichlorophenoxy acetic acid (2,4-D). The amount of growth regulators may vary according to the identity of the compound used. As an example, the concentration of 6-BA in the medium should be at least about 5 $\mu$M, and preferably at least about 10 $\mu$M, but preferably no more than 40 $\mu$M, on a basal medium such as MS, B5, White's or SH medium, all of which are well known in the art. The addition of an auxin such as IAA aids in preventing a prolonged period of undifferentiated growth by stimulating shoot formation. Auxin is preferably present in the medium in an amount of about 1–20 $\mu$M. Preferred conditions are a continuous culture temperature of about 25° C. in which the plants are exposed to cool white fluorescent light of 40 $\mu$E.ms$^{-2}$ intensity for 16 hrs./day.

Following shoot formation (about 6 weeks), shoots are excised from callus tissue and transferred to a rooting medium. A continuous culture temperature of about 25° C. is preferred in which the plants are exposed to cool white fluorescent light of 40 $\mu$E.ms$^{-2}$ intensity for 16 hrs./day. Once plantlets have become rooted (about two weeks), they may be transferred to pots and grown to maturity preferably in a greenhouse under natural light with temperatures ranging from about 10 to about 35° C. Seed is then collected from the regenerated plants, and progeny plants arising therefrom are screened.

In a preferred embodiment, regenerated plants are placed in the greenhouse and seeds collected from all fertile plants. Single plant selections are made among $R_1$ plants during field trials for such characteristics as intense red color, increased fruit number, blossom end scar size, and disease resistance. For instance in the case of one of the tomato lines of the present invention, 101–33 derived from line 101, a total of 33 somaclone lines derived from line 101 were screened for reduced blossom end scar size.

5.2. HIGH PIGMENT

The tomato lines of the present invention, have an intense attractive red color, corresponding to 42A–44A of the Colour Chart of the Royal Horticultural Society. The intense red color is due, in a preferred embodiment, to the presence of the crimson ($og^c$) allele. Alternately, the tomatoes of the present invention can also be characterized in terms of the a/b color ratio. These values may be obtained using a Hunter Color LAB (Sayama and Tigchelar, 1985, Japan J. Breed. 35:145–152), a spectrophotometer which measures the reflectance of light through the sample generally throughout the visible spectrum. Reflectance is characterized by the a and b values which are used to determine the redness of the sample via the a/b ratio. The higher the a/b ratio, the redder the tomato. In a preferred embodiment, pulp samples are prepared from fully ripe red fruit in a blender. Pulp samples are subsequently transferred to petri dishes and a and b values are obtained from the Hunter Color LAB.

The a/b values will be, under equivalent growing conditions, about 20–50% higher for the tomatoes of the present invention containing the crimson ($og^c$) allele than for varieties that have not been modified by somaclonal variation to increase their red color.

5.3. REDUCED BLOSSOM END SCAR SIZE

The parent tomato Suncoast suffers greatly from the problem of excessively large blossom end scar. Because so many otherwise good fruit must be discarded, there is a substantial decrease in marketable yield. In the tomato lines of the invention, the number of fruit with large blossom end scars is significantly reduced, so that there is little or no loss in marketable yield due to the unattractive appearance caused by this scar. The present tomatoes, in a specific embodiment, generally have a blossom end scar in the size range of about 0.03–0.11 cm$^2$ or the blossom end scar is no greater than about 60%, and is generally about 25–50%, of the blossom end scar of a given Suncoast tomato fruit grown under the same conditions. This reduction in blossom end scar size results in a concurrent increase in marketable yield on the order of 30%, solely due to the reduction of the number of tomatoes that have to be culled.

5.4. INCREASED NUMBER OF MARKETABLE FRUIT

Preferably, the marketable yield of the tomato plants of the invention is also improved due to the increase in the number of marketable fruit per plant relative to the variety Suncoast. This increase is at least as high as 25%, and may frequently be as high as 40% or more. Marketable yield in the relevant art is generally expressed as the number of 25 lb. boxes per acre. This value reflects the yield of fruit that actually would be sold and is a percentage of the total yield. Because the tomatoes of the present invention have markedly small blossom end scars, their marketable yields significantly surpass those of Suncoast.

5.5. DISEASE RESISTANCE

The tomato plants of the present invention are resistant to disease. In a specific embodiment, the tomato plants are resistant to Fusarium wilt, races 1 and 2 (believed to be conferred by $I_1$ and $I_2$ alleles), Verticillium wilt (believed to be conferred by Ve allele), and *Stemphylium solani* (believed to be conferred by Sm allele). Disease resistance may be a trait of the plants used as source material for making the somaclonal variants, or may in fact arise through somaclonal variation, starting with non-disease-resistant source material.

Tomato plants carrying the trait may be screened using procedures known in the art (see for example, Dhingra and Sinclair, 1987, Basic Plant Pathology Methods, CRC Press, Boca Raton, Fla.). Examples of such procedures, known in the art, include but are not limited to screening for an RFLP marker in tomato linked to a disease resistance allele or using an isozyme marker to detect a given disease resistance allele.

5.6. USE OF THE TOMATOES OF THE INVENTION AS SOURCE MATERIAL FOR SOMACLONAL VARIATION AND AS PARENTS IN HYBRID CROSSES

In addition to the initial lines produced by somaclonal variation, the present invention also provides a means for the production of other lines with improved characteristics, including pigment, marketable yield, blossom end scar size and disease resistance, by the use of the somaclone lines themselves as source material for somaclonal variation. These lines (i.e., plants produced from seeds having the accession number ATCC 40450 or ATCC 40506) may also be used as a parent in a cross with other tomato varieties to produce superior hybrid lines having high pigment, small blossom end scars, disease resistance, and high marketable yield. The hybrid tomato plants of the invention retain the advantageous characteristics of the parental plants, including, but not limited to, (1) producing a tomato fruit having (a) a weight of at least 140 grams; (b) a red color controlled by an $og^c$ allele; and (c) a blossom end scar from about 0.03 to about 0.11 $cm^2$; and (2) being resistant to Fusarium wilt, races 1 and 2, Verticillium wilt, and Gray Leaf Spot. Somaclonal variation has been shown to enhance the combining ability, the degree to which a parent line will express a desirable trait(s) in hybrid form, of the somaclones over the parent line, and, thus, an added benefit is also derived from the use of somaclones as a parent in a hybrid cross. The present invention, therefore, is intended to encompass not only the somaclone lines, but further any progeny, clones, somaclones, gametoclones, mutants and hybrids thereof which retain the desired characteristics.

6. EXAMPLE

6.1. SOMACLONAL VARIATION

The Suncoast variety was obtained from Dr. Jay Scott. Young, fully expanded tomato leaves were taken from five donor plants of one selection from the Suncoast variety. This selection was designated "101" herein. The leaves were sterilized by immersion in 7% Clorox for 10 minutes, and rinsed 2–3 times with sterile distilled water. Portions of the leaf tissue, approximately 5 cm×5 cm, were excised from the leaf with a sterile scalpel and aseptically transferred to a jar containing MS media (Murashige and Skoog, *Physiol. Plant*, 15:473–479 (1962)) with the addition of 6-BA at a concentration of 10 µM and IAA at a concentration of 10 µM. The explants were cultured at a temperature of 25° C. under a cool white fluorescent light of 40 $\mu E.ms^{-2}$ for 16 hrs./day. A callus mass developed after about three to four weeks and shoots were regenerated three to four weeks after callus development.

All shoots regenerated from the callus mass were transferred to a rooting media comprised of one-half strength MS media with 74 µM 3-aminopyridine and 2 µM IAA. The explants were cultured at a temperature of 25° C. under a cool white fluorescent light of 40 $\mu E.ms^{-2}$ for 16 hrs./day. One to two shoots were regenerated per explant. Plantlets were recovered on rooting medium three to twelve weeks after culture initiation.

Regenerated plants were placed in the greenhouse and seeds were collected from all fertile plants. The subsequent $R_1$ seed from each plant (now a line) were then included in field trials in various locations in Florida.

6.2. SELECTION OF 101–33

Figure 1B:
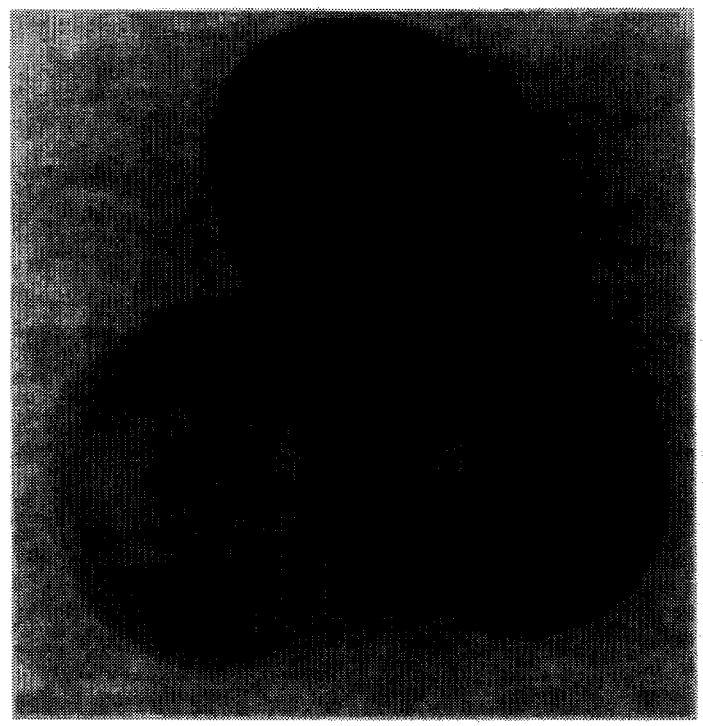
Figure 2A:
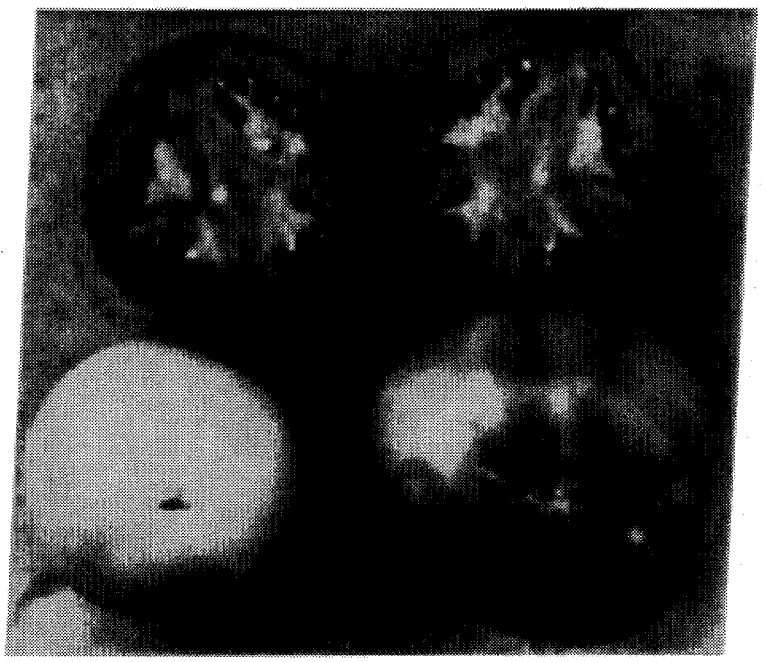
FIG. 2 shows a comparison of the blossom end scars of a tomato of the line 103–114 (top photo) and a line 103 tomato (bottom photo).
Figure 2B:
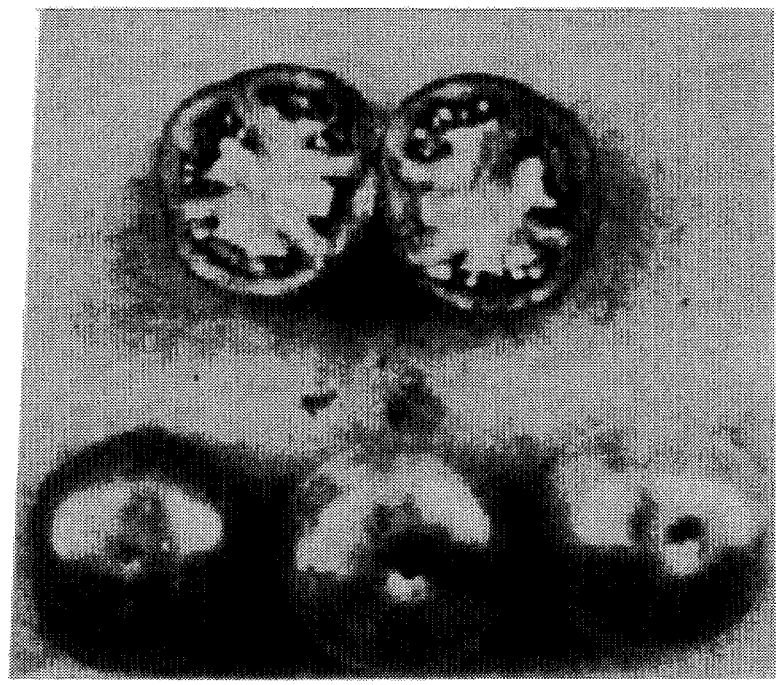

The line 101–33 was identified among a group of 101 somaclones evaluated in a field at Boca Raton, Fla. The line was conspicuous for a concentrated set of fruits (see FIG. 1) each of which had rather small blossom end scars upon visual inspection alongside fruit of Suncoast, which had obviously larger blossom end scars. 101–33 was also grown in the field at Rancocas, N.J., and here, again, the small blossom end scars relative to Suncoast were evident. The same attributes were noted when the line was evaluated in a trial conducted at Quincy, Fla. later in the same year. The line was grown in replicated plots in a trial conducted at Ruskin, Florida during late fall of that year. Observations indicated at least a 25% increase in total yield over Suncoast.

Table I, infra, represents data collected from another trial (a winter trial) conducted in Homestead, Fla. The results for wt. fruit/plant (includes full term and non-full term fruit) and no. fruit/plant (includes full term and non-full term fruit), were collected from 10 plants. The weight of fruit/plant for Suncoast was 8.15 lb. or 3.70 kg. Results for scar size and fruit diameter were obtained from 10 full term fruit randomly selected from all fruit harvested in the trial.

TABLE I

Mean Yield and Fruit Quality Measurements, Homestead Florida

| Line | Wt. Fruit/ Plant (lb.)[a] | No. Fruit/ Plant[a] | Blossom Scar Size $(cm^2)$[b] | Fruit Diameter (cm)[b] |
|---|---|---|---|---|
| Suncoast | 8.15 | 28.50 | 0.15 | 8.97 |
| 101-33 | 11.15[c] | 44.50[c] | 0.03[c] | 8.35[c] |

[a]Includes all fruit, (full term and non-full term fruit) at the time of harvest.
[b]Blossom scar size and fruit diameter measurements were made only on full term fruits
[c]Significantly different from mean of Suncoast P < 0.01

Table II, infra, represents data from another trial (a winter trial) in Boca Raton, Florida. Results for blossom scar size are presented in terms of the grand mean (combined mean) of scar size of tomatoes obtained from two replications (two different plots). There were about 10 plants per plot. Results for scar size and fruit diameter were obtained from 10 full term fruit randomly selected from all fruit harvested in the trial.

TABLE II

Blossom Scar Size Measurements, Boca Raton, Florida

| GENOTYPE | Blossom Scar Size $(cm^2)$[a] Grand Mean of Two Replications |
|---|---|
| Suncoast | 0.307 |
| 101-33 | 0.108[b] |

[a]Blossom scar size and fruit diameter measurements were made only on full term fruits
[b]Significantly different from Suncoast: P < 0.05

Table III, infra, represents data from yet another trial. This trial was conducted in Ruskin Florida. Results for yield (wt. fruit/plant) (full term and non-full term fruit) were collected from ten plants. Results for scar size and fruit diameter were obtained from 10 full term fruit randomly selected from all fruit harvested in the trial.

TABLE III

Mean Comparisons of Ruskin, Florida Spring Tomato Trial

| PEDIGREE | WT FRUIT/ PLANT (LB.)[a] | BLOSSOM SCAR SIZE $(CM^2)$[a] | FRUIT DIAMETER (CM)[b] |
|---|---|---|---|
| 101-33 | 25.0 | 0.07 | 8.50 |
| 103-114 | 32.5 | 0.09 | 8.30 |
| Suncoast | 27.0 | 0.16 | 10.00 |

TABLE III-continued

Mean Comparisons of Ruskin, Florida Spring Tomato Trial

| PEDIGREE | WT FRUIT/ PLANT (LB.)[a] | BLOSSOM SCAR SIZE (CM$^2$)[a] | FRUIT DIAMETER (CM)[b] |
|---|---|---|---|

[a] Includes all fruit, (full term and non-full term fruit) at the time of harvest
[b] Blossom scar size and fruit diameter measurements were made only on full term fruits Blossom scar size measurements in three separate trials demonstrated a significant improvement over Suncoast. Specifically, the blossom end scar size of 101–33 was reduced by at least 40% relative to Suncoast.

6.3. SELECTION OF 103–114

The $R_1$ generation of 103–114, derived from selections of the line, 103, was initially evaluated in Puerto Rico. The line, 103, was derived from the mixed breeding population, FL7181, after two cycles of selection for uniformity in vine size, fruit size, and jointless pedicels. Single plant selections were made among plants of the 103–114 $R_1$ generation for increased number of fruit with smooth blossom ends (i.e. reduced scar size). Selection for scar size was performed by identifying fruit that exhibited a scar size that was visually relatively smaller than Suncoast. Each selection was evaluated as a line ($R_2$) in a different field in New Jersey, during the following summer, then in Ruskin, Fla. in the fall and the following spring. A total of five plants that produced fruit with a smaller blossom end scar size were selected from 25 plants. The fruit quality characteristics of this line (103–114) showed a greater range of adaptability to diverse environments than Suncoast. The new somaclone, 103–114, consistently outperformed Suncoast in locations such as central and Southern Florida, Puerto Rico, and New Jersey. Improved performance was evidenced in higher marketable yield and reduced blossom end scar size. Specifically, the blossom end scar size of 103–114 was reduced by at least 40% relative to Suncoast.

Additionally, the 103–114 plants have jointless pedicels in contrast to Suncoast. This trait is believed to be controlled by a single gene with the jointed allele being dominant over the jointless allele. The jointless allele is desired over jointed since fruit are harvested lacking stems which normally have to be manually removed prior to packing.

Seed of two tomatoes of the present invention and of Suncoast and line 103 have been deposited with the American Type Culture Collection, 12301 Parklawn Dr., Rockville, Md. 20852, under the provisions of the Budapest Treaty. The accession information is as follows:

| Tomato Line | ATCC Designation |
|---|---|
| 101-33 | 40450 |
| 103-114 | 40506 |
| Suncoast | 75236 |
| 103 | 75235 |

These deposits are made only as examples of the lines of the present invention, and are not intended to be limiting to the scope of the present claims.

The invention described and claimed herein is not to be limited in scope by the specific embodiments herein disclosed, since these embodiments are intended as illustrations of several aspects of the invention. Any equivalent embodiments are intended to be within the scope of this invention. Indeed various modifications of the invention in addition to those shown and described herein will become apparent to those skilled in the art from the foregoing description. Such modifications are also intended to fall within the scope of the appended claims.

Various references are cited herein, the disclosures of which are incorporated by reference in their entireties.

What is claimed is:

1. A hybrid tomato plant, which is a hybrid of a tomato plant produced from a seed having the accession number ATCC 40450 and a tomato plant produced from a seed having the accession number ATCC 40506, which hybrid tomato plant (1) has at least one crimson $og^c$ allele;

(2) produces a tomato fruit having
  (a) a weight of at least about 140 grams,
  (b) an a/b redness ratio of at least about 1.3, and
  (c) a blossom end scar from about 0.03 to 0.11 cm$^2$; and (3) is resistant to Fusarium wilt, races 1 and 2, Verticllium wilt, and Gray Leaf Spot.

* * * * *